United States Patent
Mishra et al.

(10) Patent No.: US 10,631,113 B2
(45) Date of Patent: Apr. 21, 2020

(54) MOBILE DEVICE BASED TECHNIQUES FOR DETECTION AND PREVENTION OF HEARING LOSS

(71) Applicant: INTEL CORPORATION, Santa Clara, CA (US)

(72) Inventors: Vikas Mishra, Bangalore (IN); Raghavendra S. Hebbalalu, Bangalore (IN); Anand V. Bodas, Bangalore (IN); Kalyan Muthukumar, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 1004 days.

(21) Appl. No.: 14/945,802

(22) Filed: Nov. 19, 2015

(65) Prior Publication Data

US 2017/0150282 A1 May 25, 2017

(51) Int. Cl.
*A61B 5/00* (2006.01)
*H04R 29/00* (2006.01)
(Continued)

(52) U.S. Cl.
CPC ........... *H04R 29/001* (2013.01); *A61B 5/121* (2013.01); *A61B 5/123* (2013.01); *A61B 5/4803* (2013.01);
(Continued)

(58) Field of Classification Search
CPC ... G10L 15/22; G10L 13/0335; G10L 15/265; A61B 5/6817; A61B 2560/0242; A61B 5/7405; A61B 5/4803
(Continued)

(56) References Cited

U.S. PATENT DOCUMENTS 6,916,291 B2 * 7/2005 Givens .................. A61B 5/121
                                                    600/559
8,275,624 B2    9/2012 Kehoe
(Continued)

FOREIGN PATENT DOCUMENTS

KR    1020120069813    6/2012

OTHER PUBLICATIONS

International Search Report for International Patent Application No. PCT/US2016/051014, dated Dec. 23, 2016, 6 pages.
(Continued)

*Primary Examiner* — May A Abouelela
(74) *Attorney, Agent, or Firm* — Finch & Maloney PLLC

(57) ABSTRACT

Techniques are provided for mobile platform based detection and prevention (or mitigation) of hearing loss. An example system may include a hearing loss indicator data generation circuit configured to measure hearing loss indicator data associated with use of the device by a user. The hearing loss indicator data may include ambient sound characteristics, user speech volume level and user volume setting of the device. The system may also include an audio context generation circuit configured to estimate context data associated with use of the device. The context data may be based on classification of audio input to the device and on the location of the device. The system may further include an interface circuit configured to collect the hearing loss indicator data and the context data over a selected time period and provide the collected data to a hearing loss analysis system at periodic intervals.

12 Claims, 9 Drawing Sheets

(51) Int. Cl.
*H04R 5/04* (2006.01)
*A61B 5/12* (2006.01)
*G16H 50/20* (2018.01)
*G06F 3/16* (2006.01)
*H04W 8/18* (2009.01)
*H04W 8/24* (2009.01)

(52) U.S. Cl.
CPC .......... *A61B 5/6803* (2013.01); *A61B 5/6898* (2013.01); *A61B 5/7264* (2013.01); *A61B 5/7275* (2013.01); *G06F 3/162* (2013.01); *G06F 3/165* (2013.01); *G16H 50/20* (2018.01); *H04R 5/04* (2013.01); *H04W 8/18* (2013.01); *H04W 8/24* (2013.01); *A61B 2560/0242* (2013.01)

(58) Field of Classification Search
USPC ...... 600/300, 301, 559; 381/56, 59; 704/271
See application file for complete search history.

(56) References Cited

U.S. PATENT DOCUMENTS

| | | | | | |
|---|---|---|---|---|---|
| 8,737,630 | B2* | 5/2014 | Chang | ................ | H04R 29/001 381/56 |
| 8,942,397 | B2* | 1/2015 | Anderson | ............ | H04R 25/50 381/316 |
| 9,167,339 | B2* | 10/2015 | Knox | ...................... | H04R 1/10 |
| 9,338,566 | B2* | 5/2016 | Flynn | .................. | H04R 25/552 |
| 2005/0256378 | A1* | 11/2005 | Takai | ................ | H04L 29/06027 600/300 |
| 2008/0125672 | A1* | 5/2008 | Burrows | ................ | A61B 5/121 600/559 |
| 2009/0177113 | A1 | 7/2009 | Cromwell | | |
| 2009/0208024 | A1 | 8/2009 | Farver | | |
| 2010/0010371 | A1* | 1/2010 | Zayfert | .................. | A61B 5/165 600/558 |
| 2010/0076756 | A1* | 3/2010 | Douglas | .............. | G10L 21/0208 704/226 |
| 2010/0100388 | A1* | 4/2010 | Kehoe | ................ | G10L 21/0364 704/271 |
| 2010/0125222 | A1* | 5/2010 | Kuo | ........................ | A61B 5/121 600/559 |
| 2010/0150387 | A1* | 6/2010 | Dijkstra | ................ | H04R 25/43 381/315 |
| 2011/0004468 | A1* | 1/2011 | Fusakawa | ............... | G10L 21/04 704/214 |
| 2011/0313315 | A1* | 12/2011 | Attias | ...................... | A61B 5/12 600/559 |
| 2013/0085411 | A1 | 4/2013 | Van Tasell | | |
| 2013/0158977 | A1* | 6/2013 | Senior | .................... | G06F 17/27 704/9 |
| 2013/0274628 | A1* | 10/2013 | Fausti | .................... | A61B 5/123 600/559 |
| 2014/0194775 | A1* | 7/2014 | Van Hasselt | ........... | A61B 5/123 600/559 |
| 2015/0256956 | A1* | 9/2015 | Jensen | .................. | H04R 25/30 381/56 |
| 2016/0165372 | A1* | 6/2016 | Weksler | ............ | H04M 1/72519 381/56 |
| 2016/0330595 | A1* | 11/2016 | Hammer | ................ | H04W 4/10 |
| 2016/0352656 | A1* | 12/2016 | Galley | .................... | H04L 51/02 |
| 2018/0020298 | A1* | 1/2018 | Courtois | ............... | H04R 25/552 |

OTHER PUBLICATIONS

"Hearing Loss Prevention", Retrieved Jun. 24, 2015, 47 pages.
Newman et al, "Hearing Safety", Retrieved Jun. 24, 2015, 27 pages.

* cited by examiner

800

810 Receiving hearing loss indicator data from one or more devices of a user. The data includes ambient sound characteristics, user speech volume level and user volume setting of the device.

820 Receiving location context data associated with use of the devices by the user.

830 Performing statistical analysis of the hearing loss indicator data and the location context data, to group the hearing loss indicator data into clusters associated with the location contexts.

840 Identifying trends in the hearing loss indicator data for each of the clusters, over a selected period of time.

850 Estimating the hearing loss of the user for each of the clusters, over the selected period of time, based on the identified trends.

FIG. 8

MOBILE DEVICE BASED TECHNIQUES FOR DETECTION AND PREVENTION OF HEARING LOSS

BACKGROUND

Although hearing loss can be a common problem for many adults as a result of natural consequences of the aging process, a condition known as Presbycusis, younger adults may also be impacted with hearing loss as a result of continuous exposure to loud noises. Hearing loss can impair a person's ability to engage with others in conversation and to safely conduct routine activities, such as driving. People with impaired hearing may also be less likely than others to participate in social activities, and may generally experience a lesser quality of life.

Unfortunately, although hearing loss is a serious problem, it often remains undiscovered until after the person has become impaired. Devices and techniques do exist for coping with hearing impairment, such as medical-grade hearing aids, various sound amplification systems, high definition voice services and voice recognition applications. These may provide some level of help after hearing loss has been diagnosed, but there are currently no existing methods for unobtrusive early detection and prevention of gradual hearing loss. At present, most people must rely on an annual or semi-annual audiometry test, typically performed in a medical setting, for early detection of hearing impairment. Such tests can be relatively inconvenient and expensive and may not be performed in a timely manner.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts, and in which:

FIG. 8 is a flowchart illustrating another methodology for hearing loss detection, in accordance with certain of the embodiments disclosed herein.

Although the following Detailed Description will proceed with reference being made to illustrative embodiments, many alternatives, modifications, and variations thereof will be apparent to those skilled in the art.

DETAILED DESCRIPTION

Generally, this disclosure provides techniques for mobile platform based detection and prevention or mitigation of user hearing loss in a relatively unobtrusive manner. The increasing use of mobile devices, such as smart phones, tablets, laptops, as well as wearable devices, may be leveraged to provide long term (e.g., days to months or more) monitoring and characterization of the noise environment to which the user is subjected as well as measurement of hearing loss symptoms or indicators. Known symptoms of hearing loss may include, for example, a gradual change in conversational behavior such as requesting others to repeat words, and raising the volume setting of the device. Other indicators include muffled speech, more rapid speech, and increased volume of speech of the user. The collected hearing loss indicator data from one or more of the user's devices, along with context information related to the usage environment, may be aggregated and analyzed, for example by a remote or cloud-based analysis system. The analysis may detect hearing loss trends linked to each context over a period of time, as will be described in greater detail below. Analysis results and suggestions may be provided to the user to enable early intervention to avoid or limit further hearing impairment. It will be appreciated that the techniques described herein provide for relatively unobtrusive monitoring, requiring little if any additional activity or effort on the part of the user, thus increasing the likelihood of successful implementation and adoption by the user. The techniques can be implemented in hardware or software or a combination thereof.

In some embodiments, hearing loss indicator data associated with use of a device is measured and context data associated with that use is estimated. The context estimation may be based, at least in part, on a classification analysis of the audio input to the device as well as the location of the device. The indicator data may include ambient sound characteristics, user speech volume level, user volume setting of the device and an estimate of the user's speech word rate. The data is collected over a selected time period and provided to a remote hearing loss analysis system at periodic intervals. The hearing loss analysis system receives this data from one or more of the user's devices and performs statistical analysis to group the hearing loss indicators into clusters associated with each context and to identify trends, as will be explained herein. Reports may be generated and provided to the user in any convenient format including email, text messaging or other suitable mechanisms.

Figure 1:
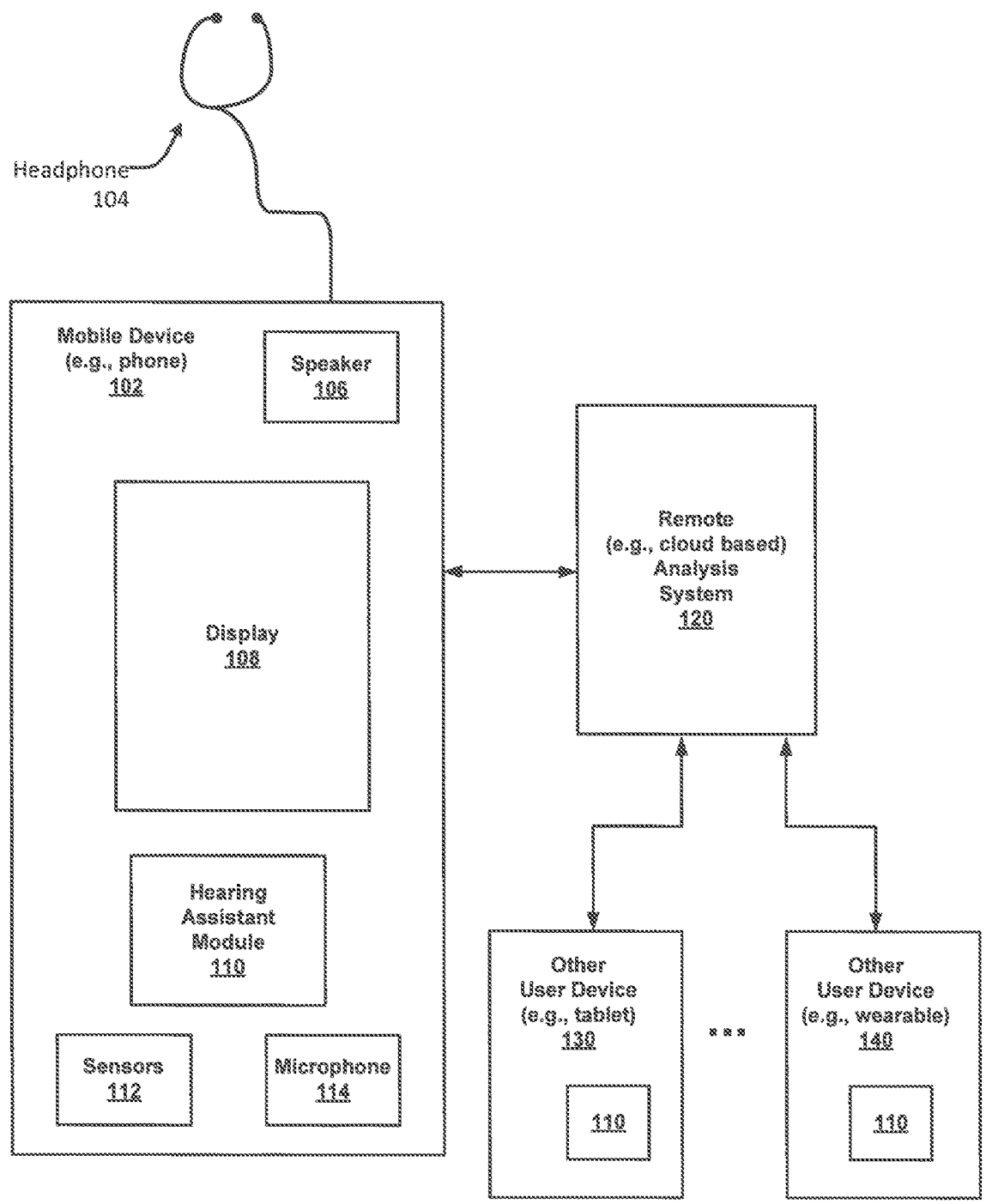
FIG. 1 is a top level system diagram of a device based hearing assistant module and a remote analysis system, configured in accordance with certain of the embodiments disclosed herein.

FIG. 1 is a top level system diagram of a device based hearing assistant module and a remote analysis system, configured in accordance with certain of the embodiments disclosed herein. The user device 102, which may be a mobile device such as a smartphone, tablet, laptop, wearable device, etc., is shown to include speaker 106, headphones 104, display element 108, microphone 114, various sensors 112 and a hearing assistant module 110, the operations of which will be described below. Additional user devices 130, 140, for example a tablet and a wearable device respectively, are also shown to include hearing assistant module 110. The remote analysis system 120 may be communicatively coupled or linked to device 102 as well as the other devices 130, 140. In some embodiments, the link may include a wired or wireless network connection to the internet and the remote analysis system 120 may be cloud-based. The various user devices 102, 130, 140 may be employed in different environments. To illustrate one example, the tablet may be used in a home environment, the laptop may be used in an office or factory environment or while traveling on an airplane, and the smartphone may be used in any of the above environments. Each environment or context may present different sources of noise and different, potentially damaging, impacts on the user's hearing.

Of course it will be appreciated that nothing in the present disclosure requires that embodiments be limited to mobile devices or that the analysis system 120 be remotely located. For example, in some embodiments, devices 102, 130, 140 may be configured as workstations and analysis system 120 may be configured as a local server on a wired network.

Figure 2:
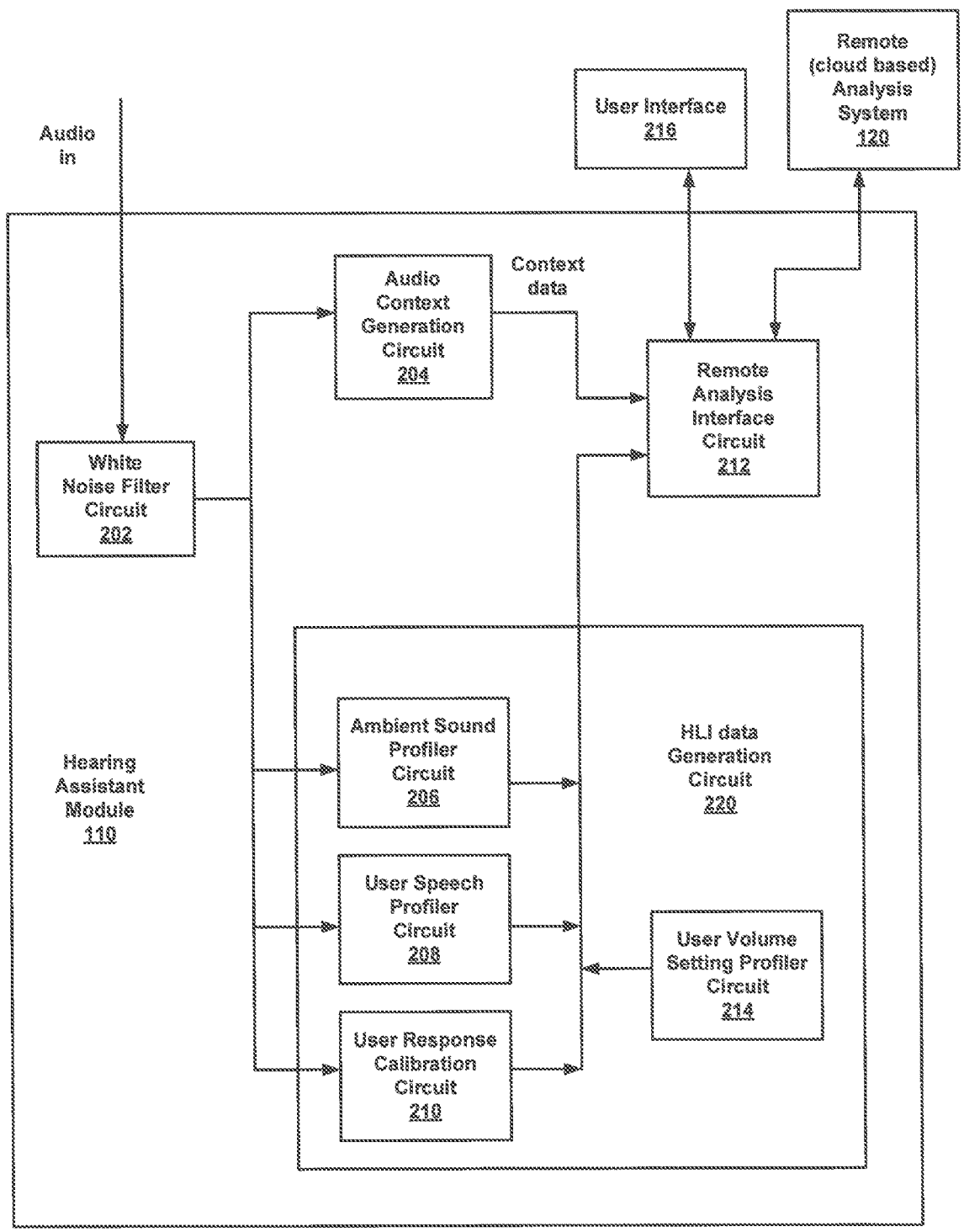
FIG. 2 is a block diagram of the hearing assistant module, configured in accordance with certain of the embodiments disclosed herein.

FIG. 2 is a block diagram of the hearing assistant module 110, configured in accordance with certain of the embodiments disclosed herein. The hearing assistant module 110 is shown to include a white noise filter circuit 202, an audio context generation circuit 204, a hearing loss indicator (HLI) data generation circuit 220 and a remote analysis interface circuit 212. The HLI data generation circuit 220 is shown to further include an ambient sound profiler circuit 206, a user speech profiler circuit 208, a user response calibration circuit 210 and a user volume setting profiler circuit 214.

The white noise filter circuit 202 may be configured to reduce white noise from the audio input stream being provided to the hearing assistant module 110. The audio input stream may include, for example, the user's voice and ambient sound from microphone 114, audio generated from applications on the device 102, or audio received from other parties on a phone call. Removal or reduction of white noise may improve subsequent analysis of the audio signal.

The hearing loss indicator data generation circuit 220 may be configured to measure hearing loss indicators associated with use of the device by the user. Indicators of hearing loss may include, for example, ambient sound characteristics, user speech volume level and word rate, user adjustments of device volume and user requests for repetition from other parties on a phone call. Thus, ambient sound profiler circuit 206 may be configured to characterize the noise environment to which the user is subjected. This characterization may include tracking the noise level, for example in decibels (dB), along with duration of exposure, since relatively high levels of ambient noise over extended periods of time may result in hearing impairment.

User speech profiler circuit 208 may be configured to characterize the speech volume of the user (and/or other speakers, for example participating in a phone conversation). User speech profiler circuit 208 may also be configured to monitor the volume levels of the user in response to selected keyphrases like "hello," or "Ok Google," which may serve as a convenient/stable benchmark for comparisons over relatively longer periods of time. User speech profiler circuit 208 may also be configured to monitor the speech rate or word rate of the user. In some embodiments, user speech profiler circuit 208 may also be configured to detect requests by the user for other parties to repeat themselves, for example on a phone call.

User volume setting profiler circuit 214 may be configured to monitor the volume level set by the user, over time, for various applications such as for phone calls, virtual assistant interaction, alert sounds and media playback, etc.

User response calibration circuit 210 may be configured to provide calibration of user responses to selected standard keywords or keyphrases, in a relatively unobtrusive manner. For example, a standard or user selected keyword or phrase like "Ok Google" may produce a standard feedback signal, like a "ding" sound at a known volume level, and the user response to that sound (e.g., adjusting device volume, or performing some action) may be monitored.

Audio context generation circuit 204 may be configured to estimate context or environment data associated with use of the device by the user. Examples of context may include, but not be limited to, a business meeting environment, a voice phone call, a work environment, a home environment, a factory environment and an entertainment environment. The context data estimation is based, at least in part, on classification of the type of audio input to the device (e.g., speech, music, crowd noise, silence, etc.) as well as the location of the device. The operation of audio context generation circuit 204 will be described in greater detail in connection with FIG. 3.

The remote analysis interface circuit 212 may be configured to collect the hearing loss indicator data and the context data over a selected time period and provide that data to a hearing loss analysis system at periodic intervals. In some embodiments, the collection period may be on the order of hours, days or weeks. The remote analysis interface circuit 212 may also be configured to receive reports from the hearing loss analysis system. The reports may include an estimate of user hearing loss and recommended actions to reduce further loss based on an analysis of the collected data provided by the interface circuit over a relatively longer period of time, for example weeks to months or longer in some embodiments. The remote analysis interface circuit 212 may also be configured to provide these reports to the user of the device, in any convenient format, for example through user interface 216. The reports may appear as visual and/or audio alerts through display 108 and/or speaker 106 and headphone 104. In some embodiments, the reports may be delivered as email or text messages through suitable message handling applications executing on the device or through other sources.

In smaller devices, such as a smartphone or wearable device, where battery capacity is more limited and power usage can be a critical factor, the device side systems and circuits described herein may be configured to run in a low-power mode of the device. Such a low power mode may be implemented in specialized hardware as part of a system-on-a-chip (SoC) architecture.

Figure 3:
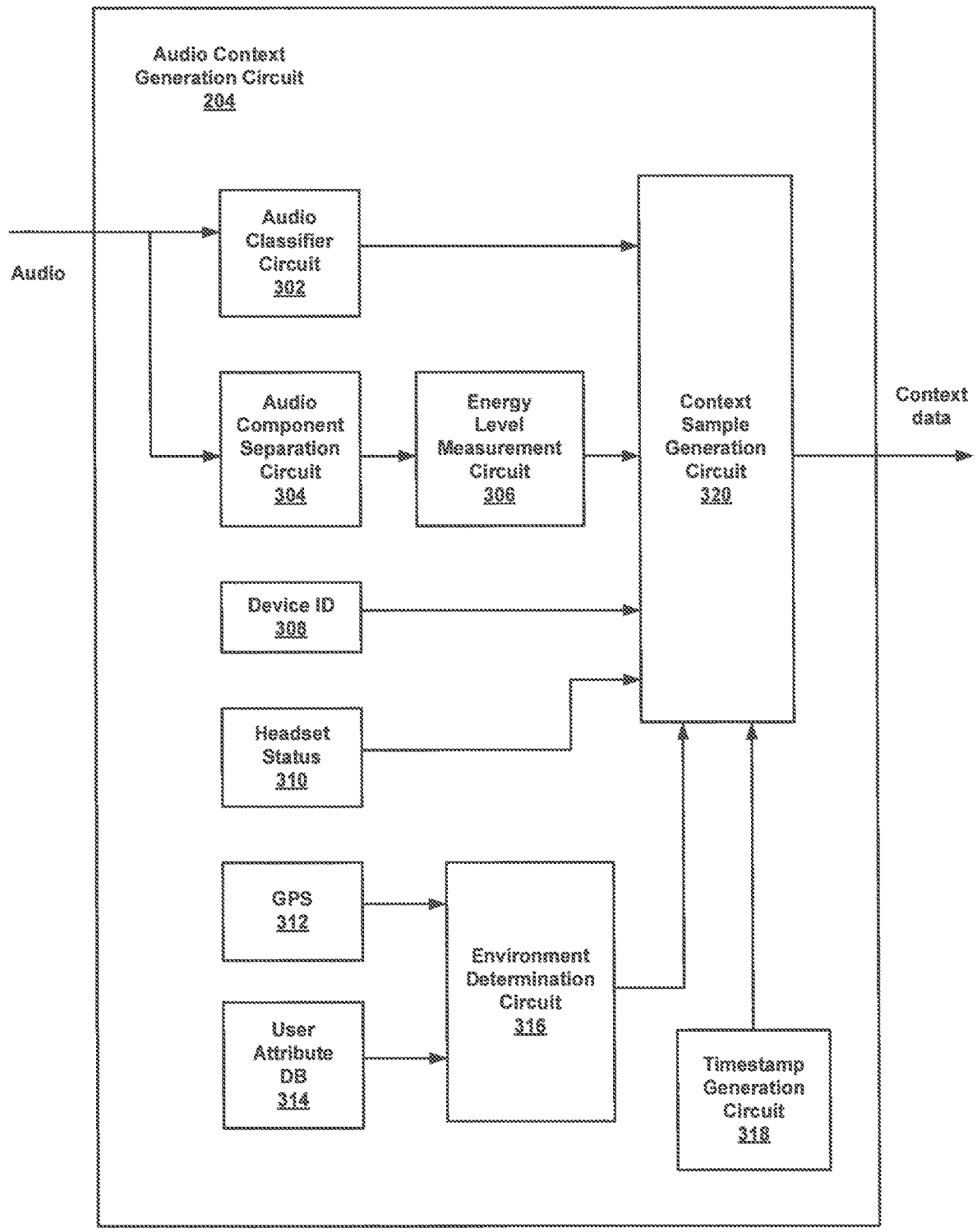
FIG. 3 is a more detailed block diagram of the audio context generation circuit component of the hearing assistant module, configured in accordance with certain of the embodiments disclosed herein.

FIG. 3 is a more detailed block diagram of the audio context generation circuit component 204 of the hearing assistant module 110, configured in accordance with certain of the embodiments disclosed herein. The audio context generation circuit 204 is shown to include a number of sub-circuits or operational components as shown. Audio classifier circuit 302 may be configured to classify the audio input into one or more categories such as, for example, speech, music, crowd noise or silence. Knowledge of the classification of audio type may improve the estimation of the audio context. For example music and/or crowd noise may be more associated with an entertainment venue such as a concert while silence may be more associated with a home environment. The classification may be performed using known techniques in light of the present disclosure. In some embodiments, for example, classification may be performed using Mel-Frequency Cepstral Analysis, to encode features from the audio signal, and Gaussian Mixture Models to cluster those features into classifications.

Audio component separation circuit 304 may be configured to separate the audio input into components such as ambient noise, speech, music, etc. so that energy level measurement circuit 306 can measure the energy associated with each component. Knowledge of the relative strengths of each audio component may also contribute to improvement of the estimation of the audio context. In some embodiments, the user's speech component may be identified based on a calibrated model of the user's voice that may be updated and refined periodically, for example by user response calibration circuit 210, as described previously.

Environment determination circuit 316 may be configured to further estimate the user's current context or environment based on location data provided by global positioning system (GPS) circuit 312 and further based on data provided by user attribute database 314. For example, the GPS 312 may provide a location indicating that the user is at a known location such as a work office, or it may indicate that the user is on a road and therefore probably commuting. The user attribute database 314 may include, for example, the user's calendar or social media data, which might indicate that the user is expected to be at a specified location at a given time. Such information may then be matched against the current time provided by a clock circuit (not shown) on the device. As another example, the user attribute database 314 may include an address book which may allow the current GPS location to be matched up to a known place such as an office or home.

Additional sensors 112 of the device 102 may also provide data useful to environment determination circuit 316. For example a gyroscope and/or accelerometer may provide data indicative of the motion or speed of the user, for example whether running, walking or stationary. As another example, light sensors may provide information as to whether the user is indoors (e.g. in a dark room) or outdoors in sunlight. These sorts of additional factors may be used to refine the estimate of the user's environment.

Context sample generation circuit may be configured to aggregate the information described above, associated with the components of audio context generation circuit 204, into a timestamped context data sample. The context data sample may also include a device ID 308 to identify the user device (e.g., smartphone, laptop, tablet, etc.). The context data sample may also include headset status 310 to indicate which audio sources are being used, such as, for example, the speaker 106, microphone 114, wired headphones 104, a wireless headset and/or a Bluetooth device, etc. As can be seen a context may include numerous parameters. One example of a context may be illustrated as follows: "the user is at home, talking on a smartphone, using a specific headset, in a voice call, with a specific other party, with a specific background noise level, at a specific time of day."

Figure 4:
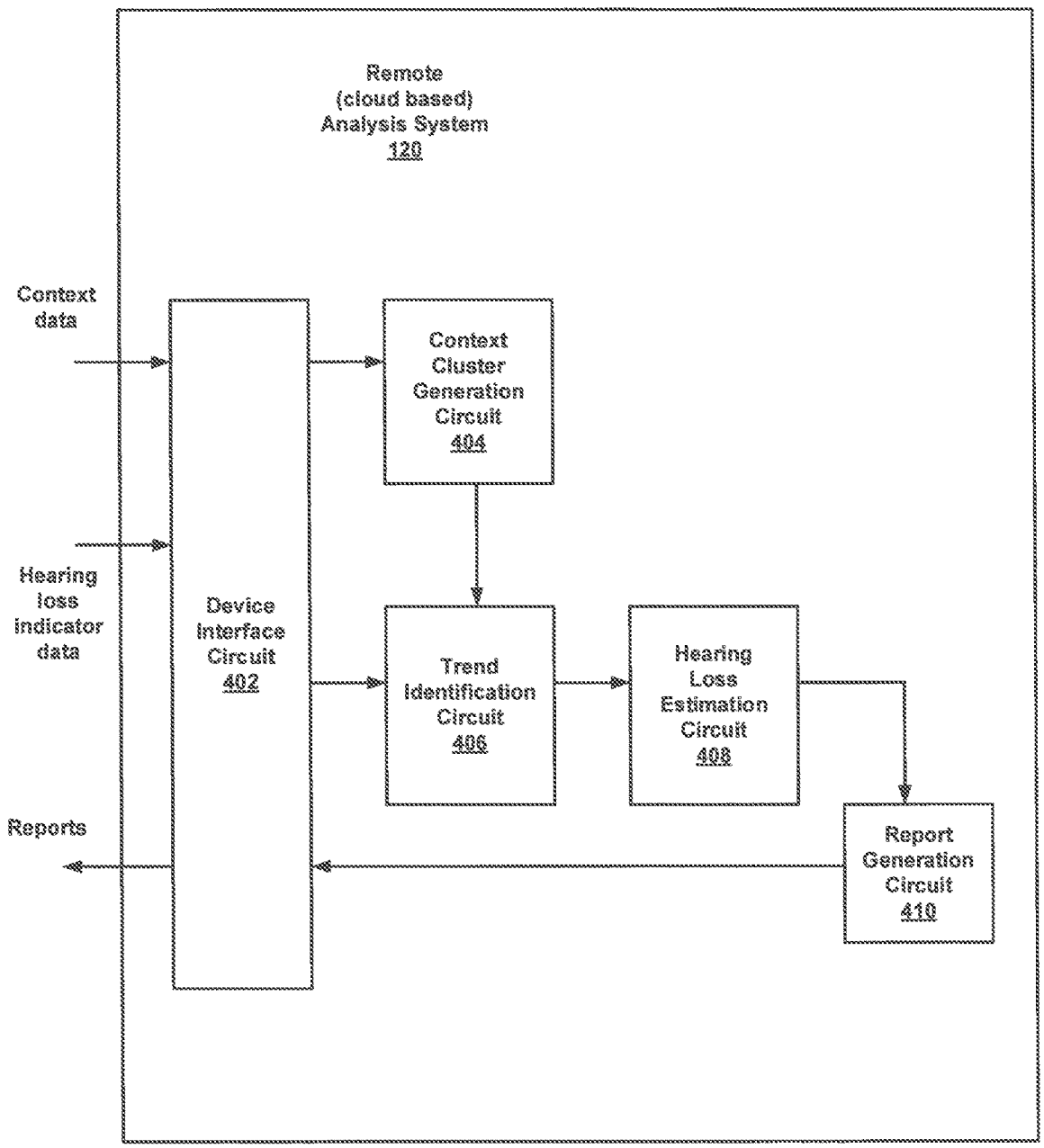
FIG. 4 is a block diagram of the remote analysis system, configured in accordance with certain of the embodiments disclosed herein.

FIG. 4 is a block diagram of the remote analysis system 120, configured in accordance with certain of the embodiments disclosed herein. The remote analysis system 120 is configured to recognize trends in hearing loss indicators, associated with usage contexts, received from the various user devices over relatively long periods of time. In some embodiments, the remote analysis system 120 is a cloud-based or internet-based system and may be configured to provide hearing loss detection services to multiple users.

The remote analysis system 120 is shown to include a device interface circuit 402, a context cluster generation circuit 404, a trend identification circuit 406, a hearing loss estimation circuit 408 and a report generation circuit 410.

The device interface circuit 402 may be configured to provide communication between the analysis system 120 and each of the one or more user devices 102, 130, 140. For example, device interface circuit 402 may receive hearing loss indicator data and context data from the user devices and may provide analysis reports back to the devices.

The context cluster generation circuit 404 may be configured to perform statistical analysis on the hearing loss indicator data and the context data to group the hearing loss indicator data into clusters associated with the environmental contexts. Contexts will generally be unique for each user. For example the context for a factory technician in a city will typically be very different from the context for a school teacher in a small town.

Figure 5:
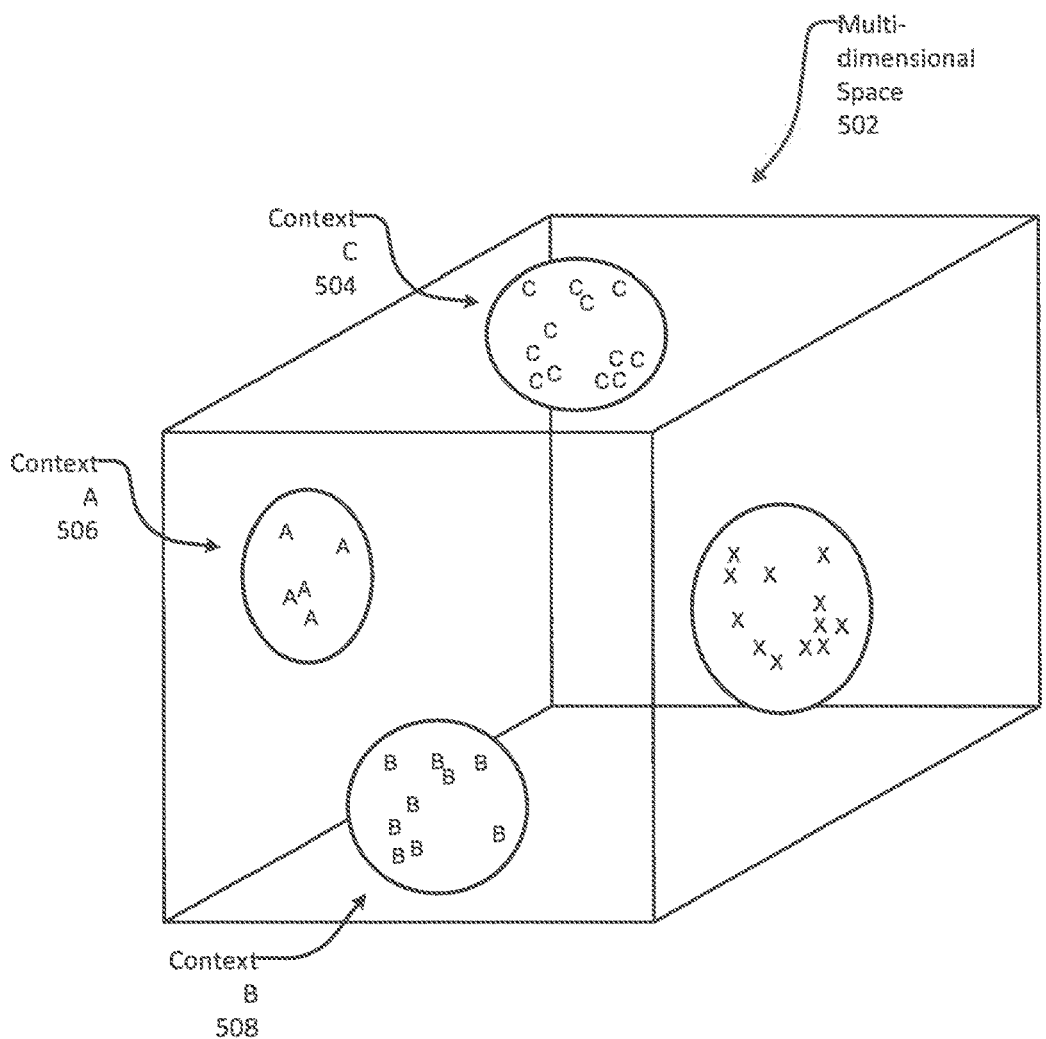
FIG. 5 illustrates context clustering associated with a hearing loss detection system, configured in accordance with certain of the embodiments disclosed herein.

The statistical analysis may be performed using known techniques in light of the present disclosure. In some embodiments, for example, the statistical analysis may be performed using K-means clustering (an unsupervised learning algorithm used to cluster data) and principal component analysis to identify patterns and reduce the dimensionality of the clusters. FIG. 5 illustrates an example of context clustering or separation in a multi-dimensional space 502 (although only 3 dimensions are shown for simplicity). Each dimension may correspond to the type of data produced from each component of the audio context generation circuit 204 previously described. For example, one of the dimensions might correspond to the audio classification, another dimension might correspond to the device ID and yet another dimension may correspond to the location. Context A 506 might correspond to a voice call using a headset, at home, with a low noise background. Context B 508 might correspond to a music playback through a headset, at a public location, with high noise background. Context C 504 might correspond to a high ambient noise environment in a factory.

Figure 6:
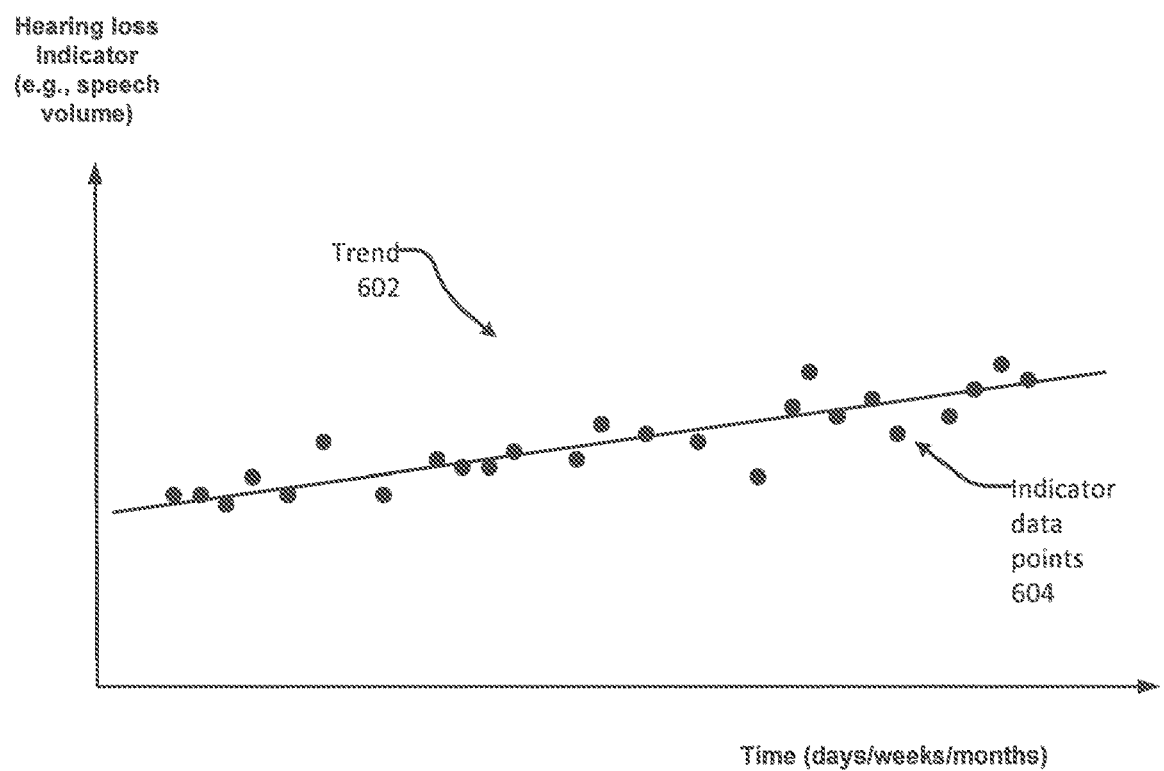
FIG. 6 illustrates a hearing loss indicator trend associated with a hearing loss detection system, configured in accordance with certain of the embodiments disclosed herein.

The trend identification circuit 406 may be configured to identify trends in the hearing loss indicator data for each of the generated clusters over a selected period of time. In some embodiments, the selected period of time may be on the order of weeks or months or more. The trends may be analyzed and anomalies removed. FIG. 6 illustrates an example of a hearing loss indicator trend 602 based on indicator data points 604 which, in this example, may be associated with user speech volume and which have been associated or separated out to a specific context cluster. The upward trend as shown may predict possible hearing impairment over a period of time. Additional trends from the multiple hearing loss indicators, separated out to the multiple contexts may be collated and analyzed, for example by hearing loss estimation circuit 408.

The hearing loss estimation circuit 408 may be configured to estimate hearing loss of the user for each of the environment contexts, over the selected period of time, based on the identified trends. In some embodiments, an initial baseline of the hearing loss indicators $\{id1, id2, id3, \ldots\}$ may be obtained by averaging the values of each indicator (after removing anomalies) during a learning or calibration phase (e.g., the first month). The baseline may referred to as: $\{avg\_id1, avg\_id2, avg\_id3, \ldots\}$. Weighting factors $\{w1, w2, w3, \ldots\}$, may be assigned and applied to each indicator, for example based on the relative importance of that indicator compared to other indicators. The baseline score may be calculated as:

$$\text{baseline\_score} = w1 * avg\_id1 + w2 * avg\_id2 + w3 * avg\_id3 + \ldots$$

As new values of the hearing loss indicators are received over time, a similar calculation may be performed. For example:

new_score=$w1$*new_avg_id1+$w2$*new_avg_id2+$w3$*new_avg_id3+ . . .

A percentage degradation may thus be calculated based on the new score relative to the baseline score. For example:

% degradation=100*(1−((|new_score−baseline_score|)/baseline_score)).

In a similar manner, percentage degradations may be calculated for each individual indicator, if desired. This process may, of course, be performed for each of the multiple contexts and a summary may be included in the generated report to the user.

The report generation circuit 410 may be configured to generate a report that includes the estimated hearing loss and recommended actions for the user based on the estimated hearing loss and environment contexts. In some embodiments, reports may include personalized trends of hearing and speech levels, a percentage degradation of hearing based on a weighted measure of multiple trends or indicators and a profile or characterization of the ambient noise that the user is exposed to (as well as changes over time). The reports may further include personalized advice to suggest that the user change behaviors or take other actions that could improve their hearing experience, such as, for example, wearing hearing protection in noisy environments, getting an audiometry test or seeking medical attention.

Methodology

Figure 7:
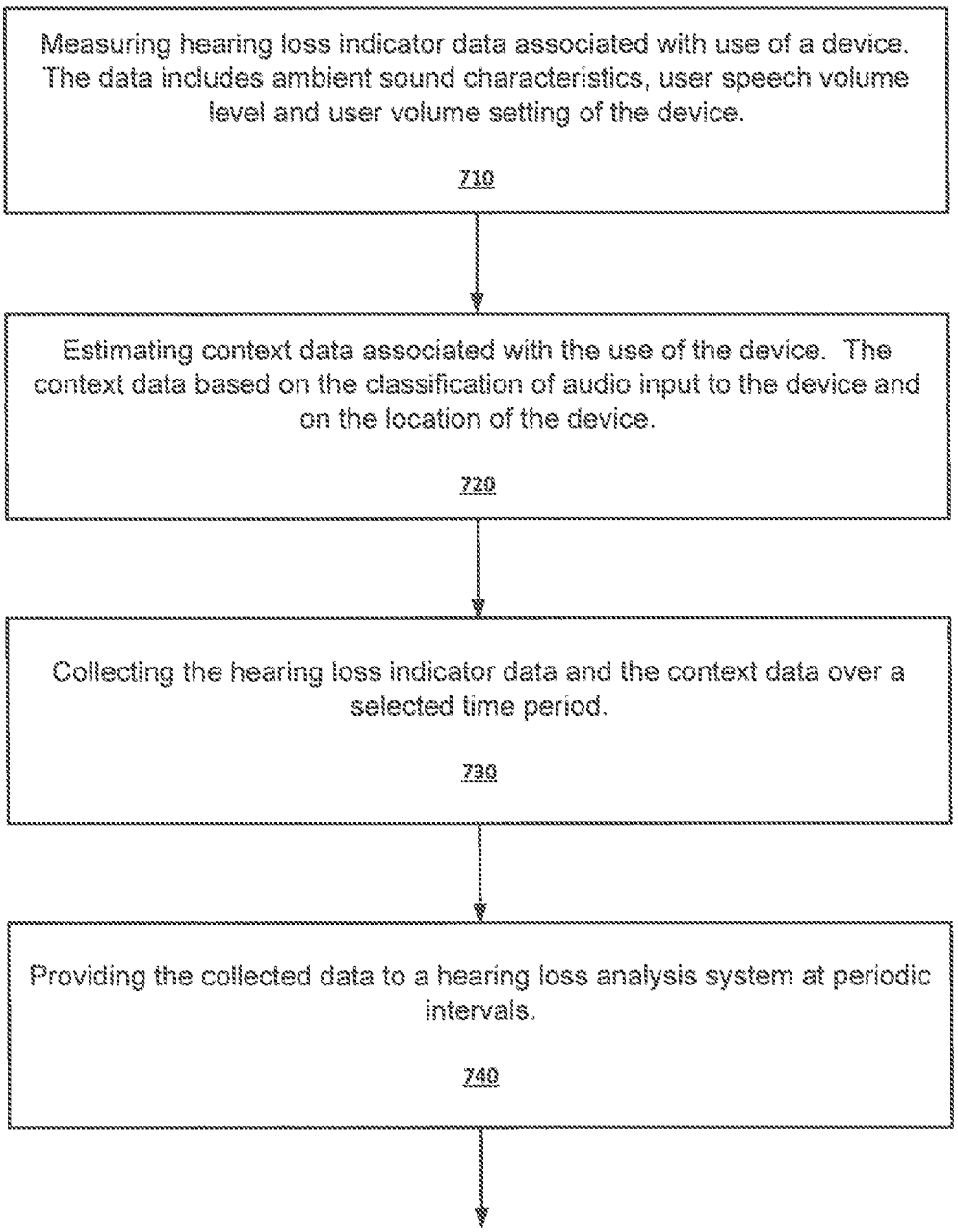
FIG. 7 is a flowchart illustrating a methodology for hearing loss detection, in accordance with certain of the embodiments disclosed herein.

FIG. 7 is a flowchart illustrating an example method 700 for detection of hearing loss of a user of a device, in accordance with an embodiment of the present disclosure. As can be seen, example method 700 includes a number of phases and sub-processes, the sequence of which may vary from one embodiment to another. However, when considered in the aggregate, these phases and sub-processes form a hearing loss detection process in accordance with certain of the embodiments disclosed herein. These embodiments can be implemented, for example using the system architecture illustrated in FIGS. 2 and 3, as described above. However other system architectures can be used in other embodiments, as will be apparent in light of this disclosure. To this end, the correlation of the various functions shown in FIG. 7 to the specific components illustrated in FIGS. 2 and 3 is not intended to imply any structural and/or use limitations. Rather other embodiments may include, for example, varying degrees of integration wherein multiple functionalities are effectively performed by one system. For example, in an alternative embodiment a single module can be used to perform all of the functions of method 700. Thus other embodiments may have fewer or more modules and/or sub-modules depending on the granularity of implementation. Numerous variations and alternative configurations will be apparent in light of this disclosure.

As illustrated in FIG. 7, in one embodiment hearing loss detection method 700 commences by measuring, at operation 710, hearing loss indicator data associated with use of the device by the user. The hearing loss indicator data may include, for example, ambient sound characteristics, user speech volume level and user volume setting of the device.

Next, at operation 720, context data associated with use of the device is estimated. The context data may be related, for example, to the location or environment in which the device is being used. The context data is based on classification of the type of audio input to the device as well as an estimate of the geographical location of the device.

At operation 730, the hearing loss indicator data and the context data is collected over a selected time period, for example hours or days. At operation 740, the collected data is provided to a hearing loss analysis system, for example a remote or cloud-based system, at periodic intervals. This is to allow the remote analysis system to aggregate the data with additional data, provided from other devices or platforms of the user, over a relatively longer time frame (e.g., weeks or months) to estimate user hearing loss.

Of course, in some embodiments, additional operations may be performed, as previously described in connection with the system. These additional operations may include, for example, receiving a hearing loss analysis report back from the remote analysis system and providing the report to the user in any suitable format. Additionally, in some embodiments, the hearing loss indicator data may further include an estimated word rate of the user's speech and a count of requests by the user for repetition of words, phrases or speech from another party.

FIG. 8 is a flowchart illustrating another example method 800 for detection of hearing loss of a user of a device, in accordance with an embodiment of the present disclosure. As can be seen, example method 800 includes a number of phases and sub-processes, the sequence of which may vary from one embodiment to another. As previously described, in connection with FIG. 7 above, when considered in the aggregate, these phases and sub-processes form a hearing loss detection process in accordance with certain of the embodiments disclosed herein. These embodiments can be implemented, for example using the system architecture illustrated in FIG. 4; however other system architectures can be used in other embodiments, as will be apparent in light of this disclosure. To this end, the correlation of the various functions shown in FIG. 8 to the specific components illustrated in FIG. 4 is not intended to imply any structural and/or use limitations. Rather other embodiments may include, for example, varying degrees of integration wherein multiple functionalities are effectively performed by one system. For example, in an alternative embodiment a single module can be used to perform all of the functions of method 800. Thus other embodiments may have fewer or more modules and/or sub-modules depending on the granularity of implementation.

As illustrated in FIG. 8, in one embodiment hearing loss detection method 800 commences by receiving, at operation 810, hearing loss indicator data from one or more devices of a user. The hearing loss indicator data is associated with use of each device by the user and may include ambient sound characteristics, user speech volume level and user volume setting of the device. Next, at operation 820, context data associated with the device use is received. The context may be associated with environments such as, for example, a meeting environment, a voice phone call, a work environment, a home environment or an entertainment environment.

At operation 830, statistical analysis is performed on the hearing loss indicator data and the context data, to group the hearing loss indicator data into clusters associated with the contexts. At operation 840, trends are identified in the hearing loss indicator data, over a selected period of time, for each of the generated clusters. In some embodiments, the time period may be on the order of weeks or months. At operation 850, user hearing loss is estimated for each of the clusters or contexts, over the selected period of time, based on the identified trends.

Of course, in some embodiments, additional operations may be performed, as previously described in connection with the system. These additional operations may include, for example, generating a report that includes the estimated hearing loss and recommended actions for the user to mitigate or prevent further loss.

Example System

Figure 9:
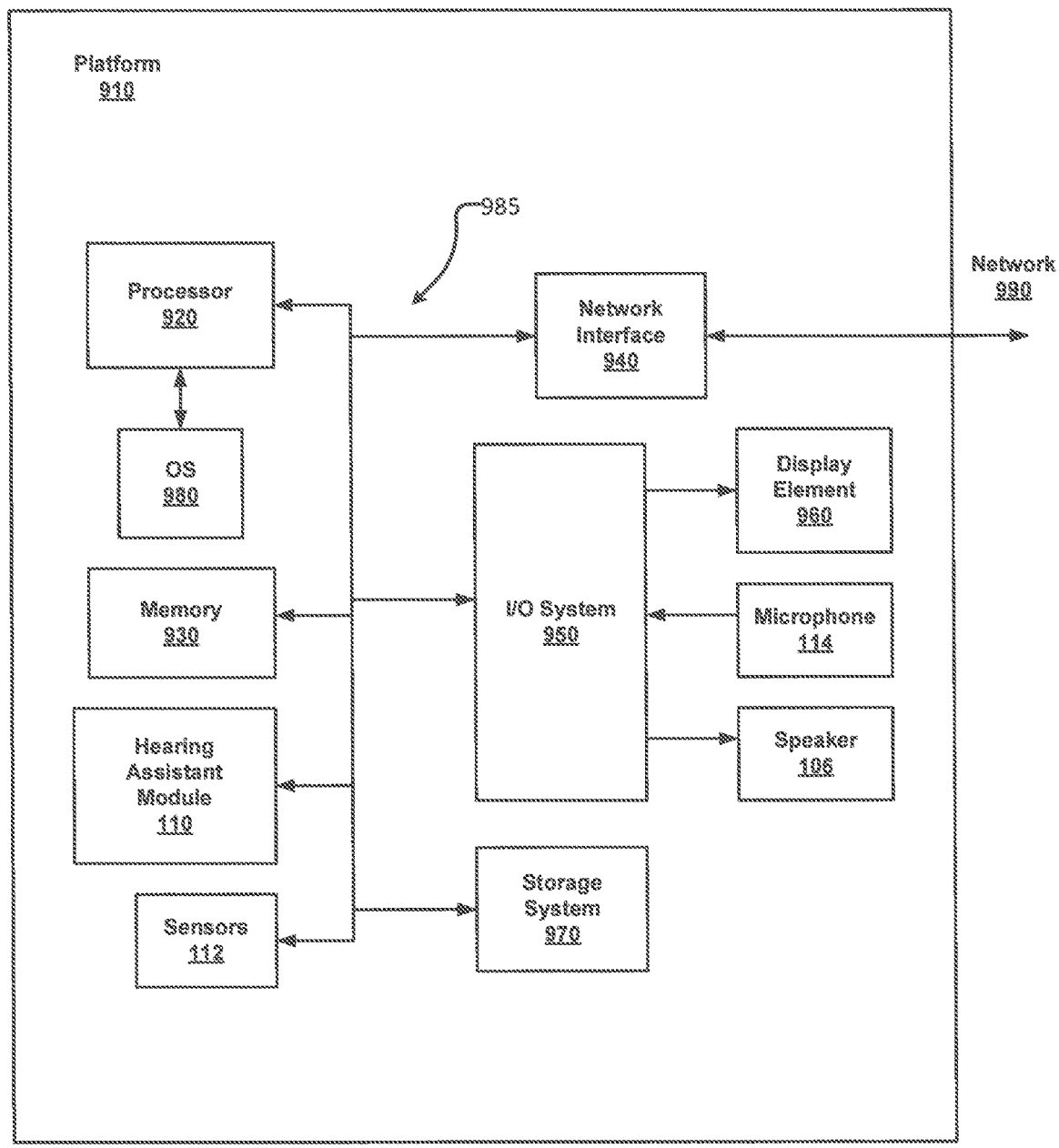
FIG. 9 is a block diagram schematically illustrating a system platform to carry out hearing loss detection, configured in accordance with certain of the embodiments disclosed herein.

FIG. 9 illustrates an example system 900 that may carry out data collection and analysis for detection and prevention or mitigation of hearing loss, as described herein. In some embodiments, system 900 comprises a platform 910 which may host, or otherwise be incorporated into, a personal computer, workstation, laptop computer, ultra-laptop computer, tablet, touchpad, portable computer, handheld computer, palmtop computer, personal digital assistant (PDA), cellular telephone, combination cellular telephone and PDA, television, smart device (for example, smartphone, smart tablet or smart television), mobile internet device (MID), messaging device, data communication device, and so forth. Any combination of different devices may be used in certain embodiments.

In some embodiments, platform 910 may comprise any combination of a processor 920, a memory 930, a hearing assistant module 110, a collection of sensors 112, a network interface 940, an input/output (I/O) system 950, a display element 960, a microphone 114, a speaker 106 and a storage system 970. As can be further seen, a bus and/or interconnect 985 is also provided to allow for communication between the various components listed above and/or other components not shown. Platform 910 can be coupled to a network 990 through network interface 940 to allow for communications with other computing devices, platforms or resources, including the remote (e.g., cloud-based) hearing loss analysis system 120 (not shown). Other componentry and functionality not reflected in the block diagram of FIG. 9 will be apparent in light of this disclosure, and it will be appreciated that other embodiments are not limited to any particular hardware configuration.

Processor 920 can be any suitable processor, and may include one or more coprocessors or controllers, such as an audio processor or a graphics processing unit, to assist in control and processing operations associated with system 900. In some embodiments, the processor 920 may be implemented as any number of processor cores. The processor (or processor cores) may be any type of processor, such as, for example, a micro-processor, an embedded processor, a digital signal processor (DSP), a graphics processor (GPU), a network processor, a field programmable gate array or other device configured to execute code. The processors may be multithreaded cores in that they may include more than one hardware thread context (or "logical processor") per core. Processor 920 may be implemented as a complex instruction set computer (CISC) or a reduced instruction set computer (RISC) processor. In some embodiments, processor 920 may be configured as an x86 instruction set compatible processor.

Memory 930 can be implemented using any suitable type of digital storage including, for example, flash memory and/or random access memory (RAM). In some embodiments, the memory 930 may include various layers of memory hierarchy and/or memory caches as are known to those of skill in the art. Memory 930 may be implemented as a volatile memory device such as, but not limited to, a RAM, dynamic RAM (DRAM), or static RAM (SRAM) device. Storage system 970 may be implemented as a non-volatile storage device such as, but not limited to, one or more of a hard disk drive (HDD), a solid state drive (SSD), a universal serial bus (USB) drive, an optical disk drive, tape drive, an internal storage device, an attached storage device, flash memory, battery backed-up synchronous DRAM (SDRAM), and/or a network accessible storage device. In some embodiments, storage 970 may comprise technology to increase the storage performance enhanced protection for valuable digital media when multiple hard drives are included.

Processor 920 may be configured to execute an Operating System (OS) 980 which may comprise any suitable operating system, such as Google Android (Google Inc., Mountain View, Calif.), Microsoft Windows (Microsoft Corp., Redmond, Wash.), or Apple OS X (Apple Inc., Cupertino, Calif.). As will be appreciated in light of this disclosure, the techniques provided herein can be implemented without regard to the particular operating system provided in conjunction with system 900, and therefore may also be implemented using any suitable existing or subsequently-developed platform.

Network interface module 940 can be any appropriate network chip or chipset which allows for wired and/or wireless connection between other components of computer system 900 and/or network 990, thereby enabling system 900 to communicate with other local and/or remote computing systems, servers, and/or resources. Wired communication may conform to existing (or yet to developed) standards, such as, for example, Ethernet. Wireless communication may conform to existing (or yet to developed) standards, such as, for example, cellular communications including LTE (Long Term Evolution), Wireless Fidelity (Wi-Fi), Bluetooth, and/or Near Field Communication (NFC). Exemplary wireless networks include, but are not limited to, wireless local area networks, wireless personal area networks, wireless metropolitan area networks, cellular networks, and satellite networks.

I/O system 950 may be configured to interface between various I/O devices and other components of computer system 900. I/O devices may include, but not be limited to, a display element 960, microphone 114, speaker 106, and other devices not shown such as a keyboard, mouse, etc.

I/O system 950 may include a graphics subsystem configured to perform processing of images for display element 960. Graphics subsystem may be a graphics processing unit or a visual processing unit (VPU), for example. An analog or digital interface may be used to communicatively couple graphics subsystem and display element 960. For example, the interface may be any of a high definition multimedia interface (HDMI), DisplayPort, wireless HDMI, and/or any other suitable interface using wireless high definition compliant techniques. In some embodiment, the graphics subsystem could be integrated into processor 920 or any chipset of platform 910. In some embodiments, display element 960 may comprise any television type monitor or display. Display element 960 may comprise, for example, a computer display screen, touchscreen display, video monitor, television-like device, and/or a television. Display element 960 may be digital and/or analog. In embodiments, display element 960 may be a holographic display. Also, display element 960 may be a transparent or opaque surface that may receive a visual projection. Such projections may convey various forms of information, images, and/or objects. For example, such projections may be a visual overlay for a mobile augmented reality (MAR) application. Under the control of the OS 980 (or one or more software applications), platform 910 may display a user interface on display element 960.

It will be appreciated that in some embodiments, the various components of the system 100 may be combined or integrated in a system-on-a-chip (SoC) architecture. In some embodiments, the components may be hardware components, firmware components, software components or any suitable combination of hardware, firmware or software.

Hearing assistant module 110 is configured to measure and collect hearing loss indicator data associated with use of the platform 910 by a user. The hearing loss indicator data may include ambient sound characteristics, user speech volume level and user volume setting of the device. Hearing assistant module 110 may further be configured to estimate context data associated with use of the platform, for example based on classification of audio input and on the location of the platform, and to provide the collected data to a remote hearing loss analysis system 120, as described previously. Hearing assistant module 110 may include any or all of the components illustrated in FIGS. 2 and 3 and described above. Hearing assistant module 110 can be implemented or otherwise used in conjunction with a variety of suitable software and/or hardware that is coupled to or that otherwise forms a part of system 900. Hearing assistant module 110 can additionally or alternatively be implemented or otherwise used in conjunction with user I/O devices that are capable of providing information to, and receiving information and commands from, a user. These I/O devices may include display element 960, a textual input device such as a keyboard, and a pointer-based input device such as a mouse. Other input/output devices that may be used in other embodiments include a touchscreen, a touchpad, a speaker 106, and/or a microphone 114. Still other input/output devices can be used in other embodiments.

In some embodiments hearing assistant module 110 may be installed local to system 900, as shown in the example embodiment of FIG. 9. Alternatively, system 900 can be implemented in a client-server arrangement wherein at least some functionality associated with hearing assistant module 110, for example the remote analysis system 120, is provided to system 900 using an applet, such as a JavaScript applet, or other downloadable module. Such a remotely accessible module or sub-module can be provisioned in real-time in response to a request from a client computing system for access to a given server having resources that are of interest to the user of the client computing system. In such embodiments the server can be local to network 990 or remotely coupled to network 990 by one or more other networks and/or communication channels. In some cases access to resources on a given network or computing system may require credentials such as usernames, passwords, and/or compliance with any other suitable security mechanism.

In various embodiments, system 900 may be implemented as a wireless system, a wired system, or a combination of both. When implemented as a wireless system, system 900 may include components and interfaces suitable for communicating over a wireless shared media, such as one or more antennae, transmitters, receivers, transceivers, amplifiers, filters, control logic, and so forth. An example of wireless shared media may include portions of a wireless spectrum, such as the radio frequency spectrum and so forth. When implemented as a wired system, system 900 may include components and interfaces suitable for communicating over wired communications media, such as input/output adapters, physical connectors to connect the input/output adaptor with a corresponding wired communications medium, a network interface card (NIC), disc controller, video controller, audio controller, and so forth. Examples of wired communications media may include a wire, cable metal leads, printed circuit board (PCB), backplane, switch fabric, semiconductor material, twisted pair wire, coaxial cable, fiber optics, and so forth.

Various embodiments may be implemented using hardware elements, software elements, or a combination of both. Examples of hardware elements may include processors, microprocessors, circuits, circuit elements (for example, transistors, resistors, capacitors, inductors, and so forth), integrated circuits, ASICs, programmable logic devices, digital signal processors, FPGAs, logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still cooperate or interact with each other.

The various embodiments disclosed herein can be implemented in various forms of hardware, software, firmware, and/or special purpose processors. For example in one embodiment at least one non-transitory computer readable storage medium has instructions encoded thereon that, when executed by one or more processors, cause one or more of the methodologies disclosed herein to be implemented. The instructions can be encoded using a suitable programming language, such as C, C++, object oriented C, JavaScript, Visual Basic .NET, Beginner's All-Purpose Symbolic Instruction Code (BASIC), or alternatively, using custom or proprietary instruction sets. The instructions can be provided in the form of one or more computer software applications and/or applets that are tangibly embodied on a memory device, and that can be executed by a computer having any suitable architecture. In one embodiment, the system can be hosted on a given website and implemented, for example, using JavaScript or another suitable browser-based technology. For instance, in certain embodiments hearing assistant module 110 obtains hearing loss indicator data and environment context data by leveraging processing resources provided by a remote computer system accessible via network 990. In other embodiments the functionalities disclosed herein can be incorporated into other software applications, for example related to audio processing in any form. The computer software applications disclosed herein may include any number of different modules, sub-modules, or other components of distinct functionality, and can provide information to, or receive information from, still other components. These modules can be used, for example, to communicate with input and/or output devices such as a display screen, a touch sensitive surface, a printer, and/or any other suitable device. Other componentry and functionality not reflected in the illustrations will be apparent in light of this disclosure, and it will be appreciated that other embodiments are not limited to any particular hardware or software configuration. Thus in other embodiments system 900 may comprise additional, fewer, or alternative subcomponents as compared to those included in the example embodiment of FIG. 9.

The aforementioned non-transitory computer readable medium may be any suitable medium for storing digital information, such as a hard drive, a server, a flash memory, and/or random access memory (RAM). In alternative embodiments, the components and/or modules disclosed herein can be implemented with hardware, including gate level logic such as a field-programmable gate array (FPGA), or alternatively, a purpose-built semiconductor such as an application-specific integrated circuit (ASIC). Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Some embodiments may be implemented, for example, using a machine readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, process, or the like, and may be implemented using any suitable combination of hardware and/or software. The machine readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CR-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing," "computing," "calculating," "determining," or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

The terms "circuit" or "circuitry," as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The circuitry may include a processor and/or controller configured to execute one or more instructions to perform one or more operations described herein. The instructions may be embodied as, for example, an application, software, firmware, etc. configured to cause the circuitry to perform any of the aforementioned operations. Software may be embodied as a software package, code, instructions, instruction sets and/or data recorded on a computer-readable storage device. Software may be embodied or implemented to include any number of processes, and processes, in turn, may be embodied or implemented to include any number of threads, etc., in a hierarchical fashion. Firmware may be embodied as code, instructions or instruction sets and/or data that are hard-coded (e.g., non-volatile) in memory devices. The circuitry may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Other embodiments may be implemented as software executed by a programmable control device. As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Numerous specific details have been set forth herein to provide a thorough understanding of the embodiments. It will be understood by an ordinarily-skilled artisan, however, that the embodiments may be practiced without these specific details. In other instances, well known operations, components and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is a computer program product comprising one or more non-transitory computer readable storage mediums encoded with instructions that when executed by one or more processors cause a process for detection of hearing loss of a user of a device to be carried out. The operations comprise measuring hearing loss indicator data associated with use of the device by the user, the hearing loss indicator data comprising ambient sound characteristics, user speech volume level and user volume setting of the device. The operations further comprise estimating context data associated with the use of the device by the user, the context data based on classification of audio input to the device and further based on location of the device. The operations further comprise collecting the hearing loss indicator data and the context data over a first selected time period. The operations further comprise providing the collected data to a hearing loss analysis system at periodic intervals.

Example 2 includes the subject matter of Example 1, wherein the hearing loss indicator data further comprises an estimated word rate of the user speech and a count of requests by the user for repetition of speech from another party.

Example 3 includes the subject matter of Examples 1 and 2, further comprising receiving a report from the hearing loss analysis system, the report comprising an estimate of user hearing loss and recommended actions to reduce further loss, the report based on an analysis of the collected data provided by the device over a second selected time period.

Example 4 includes the subject matter of Examples 1-3, wherein the report is further based on an analysis of hearing loss indicator data and context data provided by other devices of the user.

Example 5 includes the subject matter of Examples 1-4, wherein the classification of audio input further comprises classifying into one or more categories comprising speech, music, crowd noise and silence.

Example 6 includes the subject matter of Examples 1-5, wherein the context data indicates an environment selected from the group consisting of a meeting environment, a voice phone call, a work environment, a home environment and an entertainment environment.

Example 7 includes the subject matter of Examples 3-6, wherein the first selected time period is less than one week and the second selected time period is greater than one week. More generally, wherein the first selected time period is shorter than the second selected time period.

Example 8 is a system for detection of hearing loss of a user of a device. The system comprises a hearing loss indicator data generation circuit to measure hearing loss indicator data associated with use of the device by the user, the hearing loss indicator data comprising ambient sound characteristics, user speech volume level and user volume setting of the device. The system further comprises an audio context generation circuit to estimate context data associated with the use of the device by the user, the context data based on classification of audio input to the device and further based on location of the device. The system further comprises an interface circuit to collect the hearing loss indicator data and the context data over a first selected time period and provide the collected data to a hearing loss analysis system at periodic intervals.

Example 9 includes the subject matter of Example 8, wherein the hearing loss indicator data further comprises an estimated word rate of the user speech and a count of requests by the user for repetition of speech from another party.

Example 10 includes the subject matter of Examples 8 and 9, wherein the interface circuit is further to receive a report from the hearing loss analysis system, the report comprising an estimate of user hearing loss and recommended actions to reduce further loss, the report based on an analysis of the collected data provided by the interface circuit over a second selected time period.

Example 11 includes the subject matter of Examples 8-10, wherein the report is further based on an analysis of hearing loss indicator data and context data provided by other devices of the user.

Example 12 includes the subject matter of Examples 8-11, wherein the audio context generation circuit is further to classify the audio input into one or more categories comprising speech, music, crowd noise and silence.

Example 13 includes the subject matter of Examples 8-12, wherein the context data indicates an environment selected from the group consisting of a meeting environment, a voice phone call, a work environment, a home environment and an entertainment environment.

Example 14 includes the subject matter of Examples 10-13, wherein the first selected time period is less than one week and the second selected time period is greater than one week. More generally, wherein the first selected time period is shorter than the second selected time period.

Example 15 is a computer program product comprising one or more non-transitory computer readable storage mediums encoded with instructions that when executed by one or more processors cause a process for detection of hearing loss of a user of a device to be carried out. The operations comprise receiving hearing loss indicator data associated with the user from one or more devices of the user, the hearing loss indicator data comprising ambient sound characteristics, user speech volume level and user volume setting of the device. The operations further comprise receiving context data associated with use of the devices by the user. The operations further comprise performing statistical analysis of the hearing loss indicator data and the context data, to group the hearing loss indicator data into clusters associated with the contexts. The operations further comprise identifying trends in the hearing loss indicator data for each of the clusters, over a selected period of time. The operations further comprise estimating the hearing loss of the user for each of the clusters, over the selected period of time, based on the identified trends.

Example 16 includes the subject matter of Example 15, further comprising generating recommended actions for the user based on the estimated hearing loss and the contexts.

Example 17 includes the subject matter of Examples 15 and 16, further comprising sending a report to the user, the report comprising the estimated hearing loss and the recommended actions.

Example 18 includes the subject matter of Examples 15-17, wherein the statistical analysis comprises K-means clustering and principal component analysis.

Example 19 includes the subject matter of Examples 15-18, wherein the hearing loss indicator data further comprises an estimated word rate of the user speech and a count of requests by the user for repetition of speech from another party.

Example 20 includes the subject matter of Examples 15-19, wherein the context data indicates an environment selected from the group consisting of a meeting environment, a voice phone call, a work environment, a home environment and an entertainment environment.

Example 21 includes the subject matter of Examples 15-20, wherein the selected period of time is greater than one week.

Example 22 is a system for detection of hearing loss of a user. The system comprises a device interface circuit to receive hearing loss indicator data associated with the user from one or more devices of the user, the hearing loss indicator data comprising ambient sound characteristics, user speech volume level and user volume setting of the device, the device interface circuit further to receive context data associated with use of the devices by the user. The system further comprises a context cluster generation circuit to perform statistical analysis of the hearing loss indicator data and the context data, to group the hearing loss indicator data into clusters associated with the contexts. The system further comprises a trend identification circuit to identify trends in the hearing loss indicator data for each of the generated clusters, over a selected period of time. The system further comprises a hearing loss estimation circuit to estimate the hearing loss of the user for each of the clusters, over the selected period of time, based on the identified trends.

Example 23 includes the subject matter of Example 22, further comprising a report generation circuit to generate a report comprising the estimated hearing loss and recommended actions for the user based on the estimated hearing loss and the contexts.

Example 24 includes the subject matter of Examples 22 and 23, wherein the device interface circuit is further to send the report to the user.

Example 25 includes the subject matter of Examples 22-24, wherein the statistical analysis comprises K-means clustering and principal component analysis.

Example 26 includes the subject matter of Examples 22-25, wherein the hearing loss indicator data further comprises an estimated word rate of the user speech and a count of requests by the user for repetition of speech from another party.

Example 27 includes the subject matter of Examples 22-26, wherein the context data indicates an environment selected from the group consisting of a meeting environment, a voice phone call, a work environment, a home environment and an entertainment environment.

Example 28 includes the subject matter of Examples 22-27, wherein the selected period of time is greater than one week.

Example 29 is a processor-implemented method for detection of hearing loss of a user of a device. The method comprises measuring, by a processor, hearing loss indicator data associated with use of the device by the user, the hearing loss indicator data comprising ambient sound characteristics, user speech volume level and user volume setting of the device. The method further comprises estimating, by a processor, context data associated with the use of the device by the user, the context data based on classification of audio input to the device and further based on location of the device. The method further comprises collecting, by a processor, the hearing loss indicator data and the context data over a first selected time period. The method further comprises providing, by a processor, the collected data to a hearing loss analysis system at periodic intervals.

Example 30 includes the subject matter of Example 29, wherein the hearing loss indicator data further comprises an estimated word rate of the user speech and a count of requests by the user for repetition of speech from another party.

Example 31 includes the subject matter of Examples 29 and 30, further comprising receiving a report from the hearing loss analysis system, the report comprising an estimate of user hearing loss and recommended actions to reduce further loss, the report based on an analysis of the collected data provided by the device over a second selected time period.

Example 32 includes the subject matter of Examples 29-31, wherein the report is further based on an analysis of hearing loss indicator data and context data provided by other devices of the user.

Example 33 includes the subject matter of Examples 29-32, wherein the classification of audio input further comprises classifying into one or more categories comprising speech, music, crowd noise and silence.

Example 34 includes the subject matter of Examples 29-33, wherein the context data indicates an environment selected from the group consisting of a meeting environment, a voice phone call, a work environment, a home environment and an entertainment environment.

Example 35 includes the subject matter of Examples 31-34, wherein the first selected time period is less than one week and the second selected time period is greater than one week. More generally, wherein the first selected time period is shorter than the second selected time period.

Example 36 is a system for detection of hearing loss of a user of a device. The system comprises a means for measuring hearing loss indicator data associated with use of the device by the user, the hearing loss indicator data comprising ambient sound characteristics, user speech volume level and user volume setting of the device. The system further comprises a means for estimating context data associated with the use of the device by the user, the context data based on classification of audio input to the device and further based on location of the device. The system further comprises a means for collecting the hearing loss indicator data and the context data over a first selected time period. The system further comprises a means for providing the collected data to a hearing loss analysis system at periodic intervals.

Example 37 includes the subject matter of Example 36, wherein the hearing loss indicator data further comprises an estimated word rate of the user speech and a count of requests by the user for repetition of speech from another party.

Example 38 includes the subject matter of Examples 36 and 37, further comprising means for receiving a report from the hearing loss analysis system, the report comprising an estimate of user hearing loss and recommended actions to reduce further loss, the report based on an analysis of the collected data provided by the device over a second selected time period.

Example 39 includes the subject matter of Examples 36-38, wherein the report is further based on an analysis of hearing loss indicator data and context data provided by other devices of the user.

Example 40 includes the subject matter of Examples 36-39, wherein the classification of audio input further comprises means for classifying into one or more categories comprising speech, music, crowd noise and silence.

Example 41 includes the subject matter of Examples 36-40, wherein the context data indicates an environment selected from the group consisting of a meeting environment, a voice phone call, a work environment, a home environment and an entertainment environment.

Example 42 includes the subject matter of Examples 38-41, wherein the first selected time period is less than one week and the second selected time period is greater than one week. More generally, wherein the first selected time period is shorter than the second selected time period.

Example 43 is a processor-implemented method for detection of hearing loss of a user of a device. The method comprises receiving, by a processor, hearing loss indicator data associated with the user from one or more devices of the user, the hearing loss indicator data comprising ambient sound characteristics, user speech volume level and user volume setting of the device. The method further comprises receiving, by a processor, context data associated with use of the devices by the user. The method further comprises performing, by a processor, statistical analysis of the hearing loss indicator data and the context data, to group the hearing loss indicator data into clusters associated with the contexts.

The method further comprises identifying, by a processor, trends in the hearing loss indicator data for each of the clusters, over a selected period of time. The method further comprises estimating, by a processor, the hearing loss of the user for each of the clusters, over the selected period of time, based on the identified trends.

Example 44 includes the subject matter of Example 43, further comprising generating recommended actions for the user based on the estimated hearing loss and the contexts.

Example 45 includes the subject matter of Examples 43 and 44, further comprising sending a report to the user, the report comprising the estimated hearing loss and the recommended actions.

Example 46 includes the subject matter of Examples 43-45, wherein the statistical analysis comprises K-means clustering and principal component analysis.

Example 47 includes the subject matter of Examples 43-46, wherein the hearing loss indicator data further comprises an estimated word rate of the user speech and a count of requests by the user for repetition of speech from another party.

Example 48 includes the subject matter of Examples 43-47, wherein the context data indicates an environment selected from the group consisting of a meeting environment, a voice phone call, a work environment, a home environment and an entertainment environment.

Example 49 includes the subject matter of Examples 43-48, wherein the selected period of time is greater than one week.

Example 50 is a system for detection of hearing loss of a user of a device. The system comprises a means for receiving hearing loss indicator data associated with the user from one or more devices of the user, the hearing loss indicator data comprising ambient sound characteristics, user speech volume level and user volume setting of the device. The system further comprises a means for receiving context data associated with use of the devices by the user. The system further comprises a means for performing statistical analysis of the hearing loss indicator data and the context data, to group the hearing loss indicator data into clusters associated with the contexts. The system further comprises a means for identifying trends in the hearing loss indicator data for each of the clusters, over a selected period of time. The system further comprises a means for estimating the hearing loss of the user for each of the clusters, over the selected period of time, based on the identified trends.

Example 51 includes the subject matter of Example 50, further comprising means for generating recommended actions for the user based on the estimated hearing loss and the contexts.

Example 52 includes the subject matter of Examples 50 and 51, further comprising means for sending a report to the user, the report comprising the estimated hearing loss and the recommended actions.

Example 53 includes the subject matter of Examples 50-52, wherein the statistical analysis comprises K-means clustering and principal component analysis.

Example 54 includes the subject matter of Examples 50-53, wherein the hearing loss indicator data further comprises an estimated word rate of the user speech and a count of requests by the user for repetition of speech from another party.

Example 55 includes the subject matter of Examples 50-54, wherein the context data indicates an environment selected from the group consisting of a meeting environment, a voice phone call, a work environment, a home environment and an entertainment environment.

Example 56 includes the subject matter of Examples 50-55, wherein the selected period of time is greater than one week.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. It is intended that the scope of the present disclosure be limited not be this detailed description, but rather by the claims appended hereto. Future filed applications claiming priority to this application may claim the disclosed subject matter in a different manner, and may generally include any set of one or more elements as variously disclosed or otherwise demonstrated herein.

What is claimed is:

1. A computer program product comprising one or more non-transitory computer readable storage mediums encoded with instructions that when executed by one or more processors cause a process to be carried out for detection of hearing loss of a user of a device, the process carried out by the one or more processors comprising:
   measuring hearing loss indicator data associated with use of the device by the user, the hearing loss indicator data comprising ambient sound characteristics, user speech volume level, and user volume setting of the device;
   determining context data associated with the use of the device by the user, the context data based on classification of audio input received from the user through a microphone of the device and further based on location of the device;
   collecting the hearing loss indicator data and the context data over a first time period; and
   providing the collected data to a hearing loss analysis system at periodic intervals, for estimation of hearing impairment of the user.

2. The computer program product of claim 1, wherein the hearing loss indicator data further comprises an estimated word rate of the user speech and a count of requests by the user for repetition of speech from another party.

3. The computer program product of claim 1, the process further comprising receiving a report from the hearing loss analysis system, the report comprising an estimate of user hearing loss and recommended actions to reduce further loss, the report based on an analysis of the collected data provided by the device over a second time period.

4. The computer program product of claim 3, wherein the report is further based on an analysis of hearing loss indicator data and context data provided by other devices of the user.

5. The computer program product of claim 1, wherein the classification of audio input comprises classifying into one or more categories comprising speech, music, crowd noise, and silence.

6. The computer program product of claim 1, wherein the context data indicates an environment selected from the group consisting of a meeting environment, a voice phone call, a work environment, a home environment, and an entertainment environment.

7. A system for detection of hearing loss of a user of a device, the system comprising:
   one or more processors;
   a hearing loss indicator data generation module, controllable and/or executable by the one or more processors, and configured to measure hearing loss indicator data associated with use of the device by the user, the hearing loss indicator data comprising ambient sound characteristics, user speech volume level, and user volume setting of the device;
   an audio context generation module, controllable and/or executable by the one or more processors, and configured to determine context data associated with the use of the device by the user, the context data based on classification of audio input received from the user through a microphone of the device and further based on location of the device; and
   an interface module, controllable and/or executable by the one or more processors, and configured to collect the hearing loss indicator data and the context data over a first time period and provide the collected data to a hearing loss analysis system at periodic intervals, for estimation of hearing impairment of the user.

8. The system of claim 7, wherein the hearing loss indicator data further comprises an estimated word rate of the user speech and a count of requests by the user for repetition of speech from another party.

9. The system of claim 7, wherein the interface module is further to receive a report from the hearing loss analysis system, the report comprising an estimate of user hearing loss and recommended actions to reduce further loss, the report based on an analysis of the collected data provided by the interface module over a second time period.

10. The system of claim 9, wherein the report is further based on an analysis of hearing loss indicator data and context data provided by other devices of the user.

11. The system of claim 7, wherein the audio context generation module is further to classify the audio input into one or more categories comprising speech, music, crowd noise, and silence.

12. The system of claim 7, wherein the context data indicates an environment selected from the group consisting of a meeting environment, a voice phone call, a work environment, a home environment, and an entertainment environment.

* * * * *